(12) United States Patent
Sati

(10) Patent No.: US 6,801,801 B1
(45) Date of Patent: Oct. 5, 2004

(54) SYSTEM AND METHOD FOR VIRTUAL REPRESENTATION OF BONES OR A BONE JOINT

(75) Inventor: Marwan Sati, Ollen (CA)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 09/562,951

(22) Filed: May 3, 2000

Related U.S. Application Data

(63) Continuation of application No. PCT/EP97/06107, filed on Nov. 5, 1997.

(51) Int. Cl.$^7$ ................................................ A61B 5/05
(52) U.S. Cl. ........................ 600/429; 606/130; 600/407
(58) Field of Search .............................. 600/407, 429; 378/20, 205; 606/130, 97

(56) References Cited

U.S. PATENT DOCUMENTS

| | | | |
|---|---|---|---|
| 5,269,290 A | * 12/1993 | Barrett et al. ................ | 128/898 |
| 5,682,886 A | 11/1997 | Delp et al. ................ | 128/653.1 |
| 5,772,594 A | * 6/1998 | Barrick ........................ | 378/20 |
| 5,792,147 A | 8/1998 | Evans et al. ................ | 606/130 |
| 6,226,548 B1 | * 5/2001 | Foley et al. ................ | 600/426 |
| 6,314,310 B1 | 11/2001 | Ben-Haim et al. .......... | 600/424 |
| 6,348,058 B1 | 2/2002 | Melkent et al. ............. | 606/130 |
| 6,498,944 B1 | 12/2002 | Ben-Haim et al. .......... | 600/407 |
| 2002/0165448 A1 | * 11/2002 | Ben-Haim et al. .......... | 600/424 |

FOREIGN PATENT DOCUMENTS

EP                    603089            6/1994

* cited by examiner

Primary Examiner—Marvin M. Lateef
Assistant Examiner—Runa Shah Qaderi
(74) Attorney, Agent, or Firm—Jones Day

(57) ABSTRACT

A system for planning a surgical operation by using virtual representation of bones and/or a bone joint is disclosed. The system includes at least two reference frames each of which having first and second ends. The first end of each reference frame is configured to be affixed to the bones. The system also includes a plurality of first electromagnetic or acoustic wave emitting devices attached to the second end of each of the reference frames. In addition, the system includes a moveable pointer having first and second ends, wherein the first end is a pointing tip configured to be positioned at a plurality of desired locations of the bones or the bone joint and a plurality of second electromagnetic or acoustic wave emitting devices attached to the second end of the moveable pointer. Furthermore, the system includes a three-dimensional localizer device. This device includes at least two sensors and a digitizing device configured to determine three-dimensional coordinates of the first ends of the reference frames and the pointing tip based on positions and orientations of the first and second electromagnetic or acoustic wave emitting devices attached to the reference frames and the moveable pointer. Preferably, at least three first and at least three second electromagnetic or acoustic wave emitting devices art used. The system also includes an image processing unit configured to generate a virtual three-dimensional surface image based on the three-dimensional coordinates of the first ends of the reference frames and the pointing tip. The virtual three-dimensional surface image includes the plurality of desired locations of the bones or the bone joint that were pointed to by the pointing tip.

45 Claims, 2 Drawing Sheets

SYSTEM AND METHOD FOR VIRTUAL REPRESENTATION OF BONES OR A BONE JOINT

This application is a continuation of PCT/EP97/06107, filed Nov. 5, 1997.

FIELD OF THE INVENTION

The present invention relates to a device to virtually represent bones or a bone joint and to a method for planning a surgical operation by using virtual representation of bones or a bone joint.

BACKGROUND OF THE INVENTION

One of the most popular knee anterior cruciate ligament reconstruction procedure is the patellar tendon bone autograft. The success of the reconstruction may depend on both the selection of the intra-articular graft position and the initial graft tension. If the insertion sites, initial tension, geometry and mechanical properties of the normal anterior cruciate ligament can be restored during reconstructive surgery, the long-term complications of an anterior cruciate ligament injury can be greatly reduced.

To determine the optimal placement of an anterior cruciate ligament graft, the concept of "isometry" has been advocated by many authors. A perfect isometry implies that there is no change in the distance between the ligament attachment points at the femur and at the tibia, and anisometric implies the opposite. An anisometry is said to exist when there is a change in the distance during knee flexion and extension. With an weak anisometry, the graft is subjected to nearly constant tensile forces. Accordingly, the risk of rupture because of excessive tensile force in extension or flexion is reduced and the knee stability is improved. Therefore, by positioning the central part of the ligament graft at the least anisometric sites, the possibility of excessive tensile is reduced.

A conventional method for computer-assisted knee anterior cruciate ligament reconstruction is shown in DESSENNE et al., "Computer-Assisted Knee Anterior Cruciate Ligament Reconstruction: First Clinical Tests," Journal of Image Guided Surgery 1:59–64 (1995). This procedure assists the surgeon in positioning the central part of the ligament graft at the least anisometric sites.

In particular, the conventional system includes a workstation and a three-dimensional optical localizer to create images that represent knee kinematics. This surgical procedure can be performed in a typical open surgery or under use of an arthroscope. In the above described version of the system, the surgeon first drills the tibia tunnel without using the computer system. The system is then used to optimize the placement of the femoral tunnel only. The method is divided into four steps:

1) A passive flexion-extension is applied to the knee by the surgeon and for about 20–50 knee positions ranging from maximal extension to maximal flexion. At each position the location of two coordinate systems represented by optical bodies that are fixed to the femur and the tibia are computed and stored.

2) A third optical pointer is used by the surgeon to interactively collect surface points arthroscopically. Once the tibia tunnel has been developed, the center of its intra-articular extremity is digitized with the pointer. Then the surgeon acquires surface points on the femoral notch. In an area that corresponds to all possible candidate points for the femoral attachment site a set of 20–100 points is digitized.

3) Anisometry maps are then computed. The result is an "anisometry map" on the femoral surface that can be presented to the surgeon as a pseudo-color image. 4) This step concludes the interactive placement of the femoral tunnel. The surgeon can now locate the least anisometric point on the femoral surface using any standard surgical tool equipped with optical bodies, i.e., a drill.

Another method of determinating anisometric points at the femur and the tibia is disclosed in the EP-A 0 603 089 CINQUIN. This method uses reference bodies attached to the bones which comprise markers that can be detected by means of an opto-electronic position finder device. Furthermore, the device comprises a pointer having markers as well so that the position of the pointer tip may be computed. For a selected point at the tibia a set of points at the femur is digitized by mean of the pointer and then that point out of the set of points is computed. This shows the most invariability in distance to the selected point at the tibia during flexion and extension of the knee joint.

SUMMARY OF THE INVENTION

The present invention provides information needed to plan an anterior cruciate ligament reconstruction. In particular, it displays a surface section of a femur and/or a tibia of a knee. It may also display a ligament and planned drill holes for a knee reconstruction procedure. The extension of the ligament in case of knee flexion and extension may be digitized for any femoral or tibial attachment points and the drill holes may be planned such that they may be used as a drill guidance during the surgical operation.

More specifically, the present invention includes a system for planning a surgical operation by using virtual representation of bones and/or a bone joint. The system includes at least two reference frames each of which having first and second ends. The first end of each reference frame is configured to be affixed to the bones. The system also includes a plurality of and preferably at least three first electromagnetic or acoustic wave emitting devices attached to the second end of each of the reference frames. In addition, the system includes a moveable pointer having first and second ends, wherein the first end is a pointing tip configured to be positioned at a plurality of desired locations of the bones or the bone joint. Also, a plurality of and preferably at least three second electromagnetic or acoustic wave emitting devices are attached to the second end of the moveable pointer. Furthermore, the system includes a three-dimensional localizer device. This device includes at least two sensors and a digitizing device configured to determine three-dimensional coordinates of the first ends of the reference frames and the pointing tip based on positions and orientations of the first and second electromagnetic or acoustic wave emitting devices that are attached to the reference frames and the moveable pointer. The system also includes an image processing unit configured to generate a virtual three-dimensional surface image based on the three-dimensional coordinates of the first ends of the reference frames and the pointing tip. The virtual three-dimensional surface image includes the plurality of desired locations of the bones or the bone joint that were pointed by the pointing tip.

The computation of the location of the reference frames and the pointing tip is preferably based on the video-grammetric analysis of the images received by at least two cameras that detect the electromagnetic waves from the emitting devices. In addition, the digitizing may be based on the computation and analysis of electromagnetic wave interference patterns detected by at least three sensors that can be three linear charge-coupled device (CCD) cameras. The image processing unit enables the generation of relevant elements such as a section of the femur or the tibia, the ligament or the femoral or tibial tunnels at or between determined points on the display. Furthermore, the image processing unit permits to display any desired and previously acquired relevant element or combination of these elements from any desired angle of observation, to display stationary or moving relevant elements and allows the representation of the ligament at the display during knee flexion and extension while the resulting extension is digitized.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE INVENTION

Figure 1:
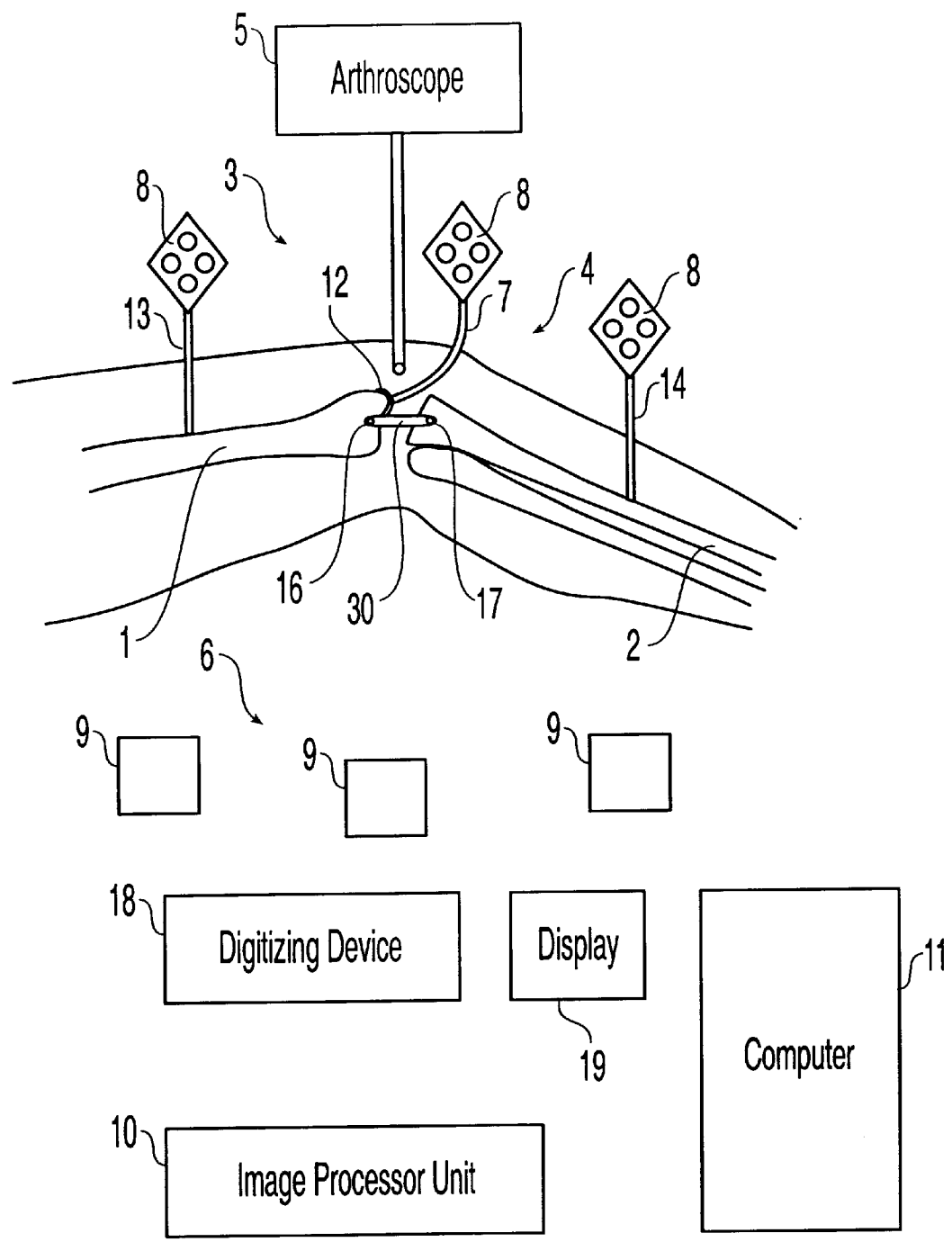
FIG. 1. shows the application of the device according to the invention in case of an anterior cruciate ligament reconstruction.

Referring to FIG. 1, a preferred system for planning a surgical operation by using virtual representation of bones and/or a bone joint is illustrated. The system includes at least two reference frames 13, 14, a moveable pointer 7, a three-dimensional digitizer 6, an image processor unit 10, a display 19 and a computer 11.

Each of the at least two reference frames 13, 14 has first and second ends. The first end of each reference frame is configured to be affixed to the bones. In FIG. 1, reference frame 13 is shown as affixed to the femur and reference frame 14 is shown as affixed to the tibia. The second end of each of the reference frames includes at least three electromagnetic or acoustic wave emitting devices 8 attached thereto. In particular, first and second at least three electromagnetic or acoustic wave emitting devices 8 are optical light sources, light emitting diodes (LED), infrared light emitting diodes, optical reflectors, acoustical transmitters or microphones.

The moveable pointer 7 also has first and second ends. The first end is a pointing tip configured to be placed at a plurality of desired locations of the bones or the bone joint. The second end of the pointer includes at least three electromagnetic or acoustic wave emitting devices 8 (similar to the devices attached to the reference frames) attached thereto. A switching device is optionally coupled to the moveable pointer 7 and other parts of the system. The switching device is configured to activate the at least three electromagnetic or acoustic wave emitting devices 8 attached to the moveable pointer 7. In operation, the surgeon would place the pointing tip at desired locations of the bones and activate the at least three electromagnetic or acoustic wave emitting devices of the moveable pointer. The emitted wave is processed at the three-dimensional localizer 6. It should be noted that it can operate without the switching device.

The three-dimensional localizer 6 includes at least two sensors 9 and a digitizing device 18. The at least two sensor are preferably Charged Couple Device (CCD) cameras. The three-dimensional localizer 18 is configured to determine three-dimensional coordinates of the first ends of the reference frames 13, 14 and the pointing tip based on positions and orientations of the first and second at least three electromagnetic or acoustic wave emitting devices 8 attached to the reference frames 13, 14 and the moveable pointer 7, respectively. It should be noted that the three-dimensional localizer 6 calculates the position and orientation of said pointers and said reference frames preferably by means of electromagnetic induction.

The image processing unit 10 is further configured to generate a virtual three-dimensional surface that includes the plurality of desired locations of the bones or the bone joint that were pointed by the pointing tip. The image processing unit may also be configured to generate virtual three-dimensional surface images from a plurality of viewing angles, to generate stationary or moving virtual three-dimensional surface images or to generate a virtual, three-dimensional representation of a connection between ligament attachment points determined by using pointer and represent therewith a ligament on the display during knee flexion and extension. Further, the position and orientation of the pointing tip in relation to the reference frames are determined by means of mechanic link devices.

The monitor 19 is configured to display the virtual three-dimensional surface generated by the image processing unit 18. An arthroscope 5 coupled to the image processing unit 18 is also provided. The image processing unit 18 is further configured to generate an image at the display 19 representing the objects observed by the arthroscope 5.

Figure 2A:
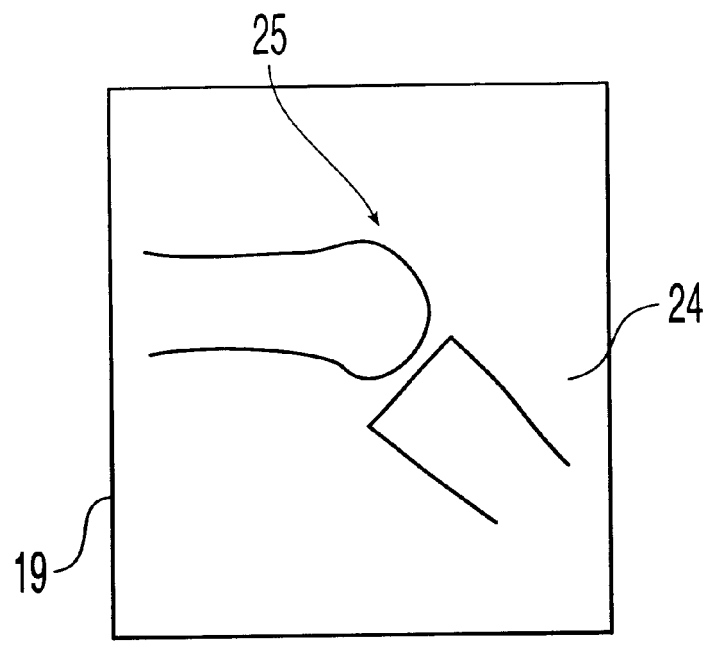
FIG. 2a shows a medio-lateral view of relevant elements.
Figure 2B:
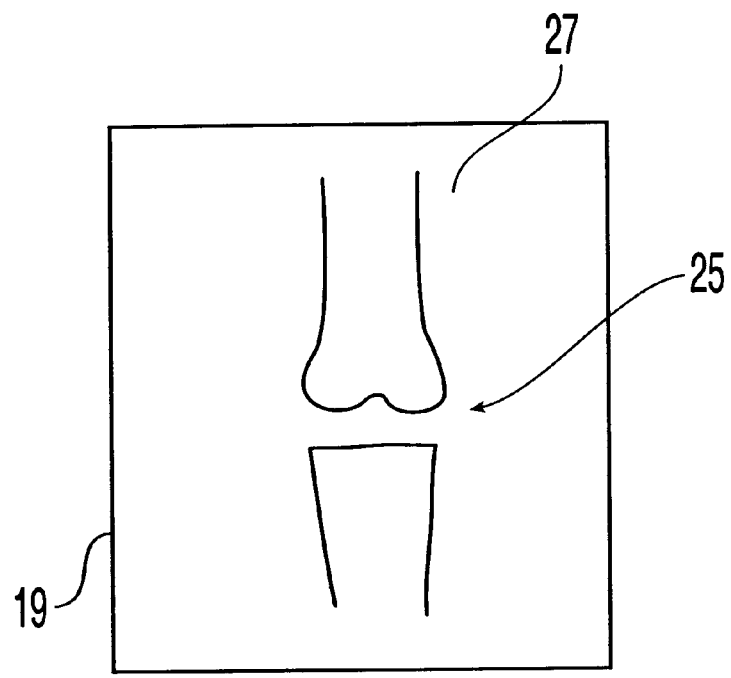
FIG. 2b shows an anterior-posterior view of relevant elements.

In operation, by using the pointer 7, arthroscope 5 and the image processing unit 10 the surgeon determines relevant elements 25 (e.g., a section of the femur 1, a section of the tibia 2, the ligament, a drill hole etc.) at or between certain points on the display 19. By use of the image processing unit 10, any desired and previously acquired relevant element 25 or combination of these elements may be shown at any desired angle and scale of observation at the display 19. For example, referring to FIG. 2a, a medio-lateral view 26 or, referring to FIG. 2b, an anterior-posterior view 27 may be chosen. Furthermore, the image processing unit 10 allows the display of stationary or moving relevant elements 25 and enables a dynamic view by using an arthroscope 5. Moreover, the image processing unit 18 enables the representation of the ligament at the display 19 during knee flexion and extension and the resulting extension of the ligament is digitized. The shifting to an anterior-posterior view also enables the surgeon to observe the ligament during knee flexion and extension and to perform a ligament impingement simulation. The tunnels 16, 17 for the attachments of the ligament 30 as well as the placement of the ligament 30 are then determined using the display 19. By viewing the drill holes at the display 19, the drill can be guided during the surgical operation.

a) attachment of reference frames 13, 14 with electromagnetic or acoustic waves emitting means 8 to the femur and to the tibia whereby the emitting means 8 attached to the reference frames 13, 14 enable a computation of reference coordinate systems by digitizing. This is based on the computation and analysis of electromagnetic wave interference patterns detected by at least three sensors 9 that can be three linear charge-coupled device (CCD) cameras. In addition, the computation of the location of the reference frames and the points can be completed based on the video-grammetric analysis of the images received by at least two CCD cameras that detect the electromagnetic waves from the emitting means 8;

b) the pointer 7 is used to digitize points which are generated by placing the pointing tip at a desired position of the bones or of the bone joint and press the switch to localize the electromagnetic or acoustic waves emitting means attached at the pointer. And, then digitizing the position and orientation of the pointing tip and the points are shown at the display 19 of the computer 11 related to a chosen reference system;

c) by means of the image processing unit 10 a virtual three-dimensional surface at the display is generated containing the points that were previously determined by the pointer 7.

d) a three-dimensional representation of the ligament is generated by using the points that were previously determined by the pointer 7;

e) a three-dimensional simulation of the ligament during flexion-extension of the knee is shown at the display and the optimal locations of the ligament attachment points and of the drill holes are planned by the surgeon;

f) by means of the desirable angle of observation a medio-lateral view or a anterior-posterior view may be chosen; and g) the different angle of observation enables the surgeon to plan the surgical operation also in view of a ligament impingement simulation.

Although the preferred embodiments of the invention have been described in the foregoing description, it will be understood that the present invention is not limited to the specific embodiments described above.

What is claimed is:

1. A system for planning a surgical operation by using virtual representation of bones and/or a bone joint, the system comprising:

at least two reference frames each of which having first and second ends, wherein the first end of each reference frame is configured to be affixed to bones;

a plurality of first electromagnetic or acoustic wave emitting devices attached to the second end of each of the reference frames;

a moveable pointer having first and second ends, wherein the first end is a pointing tip configured to directly contact bone, bone tissue or a bone joint at a plurality of desired locations;

a plurality of second electromagnetic or acoustic wave emitting devices attached to the second end of the moveable pointer;

a switching device configured to activate the second electromagnetic or acoustic wave emitting devices; and a three-dimensional localizer device comprising:
   at least two sensors; and
   a digitizing device configured to determine three-dimensional coordinates of the first ends of the reference frames and the pointing tip based on positions and orientations of the first and second at least three electromagnetic or acoustic wave emitting devices attached to the reference frames and the moveable pointer; and an image processing unit configured to generate a virtual three-dimensional surface image based on the three-dimensional coordinates of the first ends of the reference frames and the pointing tip, wherein the virtual three-dimensional surface image includes the plurality of desired locations of the bones or the bone joint that were pointed by the pointing tip.

2. The system according to claim 1 further comprising: a monitor configured to display the virtual three-dimensional surface generated by the image processing unit.

3. The system according to claim 1 wherein the image processing unit is further configured to generate virtual three-dimensional surface images from a plurality of viewing angles.

4. The system according to claim 1 wherein the image processing unit is further configured to generate stationary or moving virtual three-dimensional surface images.

5. The system according to claim 1 wherein the image processing unit is further configured to generate a virtual three-dimensional representation of a connection between ligament attachment points determined by using the pointing tip.

6. The system according to claim 1 further comprising an arthroscope coupled to the image processing unit, wherein the image processing unit is further configured to generate an image at the display representing the objects observed by the arthroscope.

7. The system according to claim 1 wherein the three-dimensional localizer device localizes the position and orientation of said pointers and said reference frames by means of electromagnetic induction.

8. The system according to claim 1 wherein at least three first and at least three second electromagnetic or acoustic wave emitting devices are present.

9. The system according to claim 1 wherein the first and second electromagnetic or acoustic wave emitting devices are optical light sources.

10. The system according to claim 1 wherein the first and second electromagnetic or acoustic wave emitting devices are light emitting diodes.

11. The system according to claim 1 wherein the first and second electromagnetic or acoustic wave emitting devices are infrared light emitting diodes.

12. The system according to claim 1 wherein the first and second electromagnetic or acoustic wave emitting devices are optical reflectors.

13. The system according to claim 1 wherein the first and second electromagnetic or acoustic wave emitting devices are acoustical transmitters.

14. The system according to claim 1 wherein the first and second electromagnetic or acoustic wave emitting devices are microphones.

15. The system according to claim 1 wherein the virtual three-dimensional surface image comprise a ligament, drill holes and previously digitized surfaces of a femur or a tibia of a knee joint.

16. The system according to claim 1 wherein the position and orientation of the pointing tip in relation to the reference frames are determined by means of mechanic link devices.

17. A method for planning a surgical operation by using virtual representation of bones or a bone joint, the method comprising:

receiving signals from a plurality of transmitters attached to a first end of each of at least two reference frames, wherein a second end of one of the at least two frames is affixed to one bone and a second end of another one of the at least two frames is affixed to a second bone;

positioning a pointing tip of a moveable pointer directly on a portion of a bone, bone tissue or a bone joint at a plurality of desired positions;

causing a plurality of electromagnetic or acoustic wave emitting devices attached on the moveable pointer to emit signals each time the pointing tip is positioned at the plurality of desired positions;

digitizing the received signals;
calculating locations of the second end of each of the at least two reference frames and the pointing tip based on the digitized signals; and
generating a virtual three-dimensional rendering of a joint formed by the bones or bone joint based on the calculated locations.

18. The method according to claim 17 further comprising displaying the images at any desired angle of observation and at any scale.

19. The method according to claim 17 further comprising generating the desirable angle of observation a medio-lateral view or an anterior-posterior view.

20. The method according to claim 17 wherein the bones are different and further comprising generating a three-dimensional representation of a connection between ligament attachment points determined by using the pointing tip.

21. The method according to claim 20 wherein one bone is a femur, the other bone is a tibia, and the femur and tibia are connected by a knee, and the method further comprises:
generating a three-dimensional simulation of the ligament during flexion-extension of the knee; and
generating optimal locations of the ligament attachment points and of drill holes, to thereby allow a surgeon to plan a knee reconstruction procedure.

22. The method according to claim 20 further comprising:
generating at least one image of relevant elements which includes a ligament and drill holes using the pointing tip at two points; and
computing a cylinder having an axis through these two points and digitized surfaces of the femur and tibia.

23. A system for preparing a three-dimensional image of at least a portion of at least one bone, the system comprising:
a pointer comprising:
a first end configured to directly engage bone, bone tissue or a bone joint;
a first plurality of electromagnetic wave emitter (EWE) spaced apart from the first end of the pointer, the first plurality of EWE and the first end of the pointer having a known spatial relationship;
a first fiducial including a second plurality of EWE; and
a localizer device, comprising:
at least two sensors configured to detect electromagnetic waves emitted by the first and second plurality of EWE;
a first processor at least configured to:
determined 3D coordinates of the first and second plurality of EWE based upon electromagnetic waves emitted by the first and second plurality of EWE and detected by the at least two sensors;
determined 3D coordinates of a location of a surface of a bone contacted with the first end of the pointer based upon (1) 3D coordinates of the first plurality of EWE determined when the first end of the pointer is in contact with the location of the surface of the bone (2) the known spatial relationship between the first end of the pointer and the first plurality of EWE and (3) 3D coordinates of the second plurality of EWE based upon electromagnetic waves emitted by the second plurality of EWE and detected by the at least two sesors; and
a second processor at least configured to generate, based upon 3D coordinates of each of a plurality of respective locations of a surface of a bone contact by the first end of the pointer, a 3D image of at least a portion of the at least one bone.

24. The system of claim 23, further comprising:
wherein the a first fiducial is configured to be attached to a bone; and
at least when the first fiducial is attached to a bone:
the first processor is configured to determine a spatial relationship between (1) a location of a surface of a bone contacted with the first end of the pointer to determine 3D coordinates of the location and (2) the second plurality of EWE.

25. The system of claim 24, wherein the first processor is configured to, upon movement of a bone having the first fiducial attached thereto from a first location to a different, new location:
determine new 3D coordinates of the second plurality of EWE based upon electromagnetic waves emitted by the second plurality of EWE and detected by the at least two sensors; and
determine new 3D coordinates of a location of a surface of the bone based upon a spatial relationship between the location of the surface of the bone and the new 3D coordinates of the second plurality of EWE.

26. The system of claim 24, further comprising:
a second fiducial configured to be attached to a second bone, the second fiducial comprising a third plurality of EWE;
wherein, at least when the second fiducial is attached to a second bone:
the at least two sensors of the localizing device are further configured to detect electromagnetic waves emitted by the third plurality of EWE of the second fiducial;
the first processor is configured to determined 3D coordinates of the third plurality of EWE based upon elelctromagnetic waves emitted by the third plurality of EWE and detected by the at least two sensors; and
the first processor is configured to determine a spatial relationship between (1) a location of a surface of a second bone contacted with the first end of the pointer to determine 3D coordinates of the location and (2) the third plurality of EWE.

27. The system of claim 26, wherein the first processor is configured to, upon movement of a second bone having the second fiducial attached thereto from a first location to a different, new location:
determine new 3D coordinates of the third plurality of EWE based upon electromagnetic waves emitted by the third plurality of EWE and detected by the at least two sensors; and
determine new 3D coordinates of a location of a surface of the second bone based upon a spatial relationship between the location of the surface of the second bone and the new 3D coordinates of the third plurality of EWE.

28. The system according to claim 23, wherein the first and second processors are the same.

29. The system according to claim 23, further comprising: a monitor configured to display the 3D image generated by the second processor.

30. The system according to claim 23, wherein the second processor is further configured to generate a 3D representation of a connection between ligament attachment points determined by using the first end of the pointer.

31. The system according to claim 23, further comprising an arthroscope coupled to the second processor, wherein the second processor is furter configured to generate an image comprising representations of objects observed via the arthroscope.

32. The system according to claim 23, wherein the 3D image comprises a ligament, drill holes and previously digitized surfaces of a femur ora tibia of a knee joint.

33. A method for generating a three-dimensional image of a surface of at least one bone, the method comprising:
   (a) attaching a first fiducial directly to a first bone, the first fiducial comprising a first plurality of electromagnetic wave emitters (EWE);
   (b) contacting a location of a surface of the first bone with a first end of a pointer;
   (c) receiving electromagnetic waves from the first plurality of EWE;
   (d) receiving electromagnetic waves from a second plurality of EWE, the second plurality of EWE and the first end of the pointer having a known spatial relationship;
   (e) determining three-dimensional (3D) coordinates of the first location of the surface of the first bone based upon the electromagnetic waves received from the first plurality of EWE, the second plurality of EWE, and the known spatial relationship between the second plurality of EWE and the first end of the pointer;
   (f) repeating the steps of contacting a location of a surface of the first bone with a first end of a pointer, receiving electromagnetic waves from the second plurality of EWE and determining three-dimensional (3D) coordinates of the location of the surface of the first bone for each of a plurality of different locations of the surface of the first bone to obtain a plurality of 3D coordinates, each of the different 3D coordinates corresponding to a respective one of the different locations of the surface of the first bone; and
   (g) generating a 3D image of the surface of the first bone based at least upon the plurality of 3D coordinates determined during the step of (f).

34. The method according to claim 33, further comprising:
   (n) determining a spatial relationship between (1) at least one of the locations of the surface of the first bone for which 3D coordinates were determined during the step of (f) and (2) the second plurality of EWE.

35. The method according to claim 34, further comprising:
   after the step of (n):
      repeating the steps of receiving electromagnetic waves from the first plurality of EWE; determining 3D coordinates of the first plurality of EWE based upon the electromagnetic waves received therefrom to obtain new 3D coordinates of the first plurality of EWE; and
      determining new 3D coordinates of the at least one location of the surface of the first bone for which at least one location the spatial relationship was determined in the step of (n), wherein the determination of the new 3D coordinates is based upon the new 3D coordinates of the first plurality of EWE and the spatial relationship between the at least one location and the first plurality of EWE.

36. The method according to claim 33, further comprising:
   (h) contacting a location of a surface of a second bone with the first end of the pointer;
   (i) receiving electromagnetic waves from the second plurality of electromagnetic wave emitters (EWE);
   (j) determining three-dimensional (3D) coordinates of the first location of the surface of the second based upon the electromagnetic waves received from the second plurality of EWE and the known spatial relationship between the second plurality of EWE and the first end of the pointer;
   (k) repeating the steps of contacting a location of a surface of the second bone with a first end of a pointer; receiving electromagnetic waves from the second plurality of EWE and determining three-dimensional (3D) coordinates of the location of the surface of the second bone for each of a plurality of different locations of the surface of the second bone to obtain a plurality of 3D coordinates, each of the 3D coordinates corresponinedg to a respective one of the different locations of the surface of the second bone; and
   (l) generating a 3D image of the surface of the second bone based at least upon the plurality of 3D coordinates determined during the step of (k).

37. The method according to claim 36, wherein the images generated in the step of (g) and the step (l) are the same image and the image comprises the surfaces of both the first and second bones.

38. The method according to claim 37, wherein the image that comprises the surfaces of both the first and second bones comprises:
   a representation of a ligament attachment point of the first bone;
   a representation of a ligament attachment point of the second bone; and
   a representation of a connection between the attachment points of the first and second bones.

39. The method according to claim 36, further comprising:
   (n) determining a spatial relationship between (1) at least one of the locations of the surface of the first bone for which 3D coordinates were determined during the step of (f) and (2) the second plurality of EWE.

40. The method according to claim 39, further comprising:
   (o) attaching a second fiducial to the second bone, the second fiducial comprising a third plurality of EWE;
   (p) receiving electromagnetic waves from the third plurality of EWE;
   (q) determining 3D coordinates of the third plurality of EWE based upon the electromagntic waves received therefrom; and
   (r) determining a spatial relationship between (1) at least one of the locations of the surface of the second bone for which 3D coordinates were determined during the step of (k) and (2) the third plurality of EWE.

41. The method according to claim 40, further comprising:
   after the step of (n):
      repeating the steps of receiving electromagnetic waves from the first plurality of EWE and determining 3D coordinates of the first plurality of EWE based upon the electromagnetic waves received therefrom to obtain new 3D coordinates of the first plurality of EWE; and
      determining new 3D coordinates of the at least one location of the surface of the first bone for which at least one location the spatial relationship was determined in the step of (n), wherein the determination of the new 3D coordinates is based upon the new 3D coordinates of the first plurality of EWE and the spatial relationship between the at least one location and the first plurality of EWE.

42. The method according to claim 41, further comprising:

after the step of (r):

repeating the steps of receiving electromagnetic waves from the first plurality of EWE; determining 3D coordinates of the first plurality of EWE based upon the electromagnetic waves received therefrom to obtain new 3D coordinates of the third plurality of EWE; and determining new 3D coordinates of the at least one location of the surface of the second bone for which at least one location the spatial relationship was determined in the step of (r), wherein the determination of the new 3D coordinates is based upon the new 3D coordinates of the third plurality of EWE and the spatial relationship between the at least one location and the third plurality of EWE.

43. The method according to claim 42, wherein the images generated in the step of (g) and the step (l) are the same image and the images comprises the surfaces of both the first and second bones.

44. The method according to claim 42, wherein one of the first and second bones is a femur, the other of the first and second bones is a tibia, and the femur and tibia are connected by a knee, and the method further comprises:

generating a three-dimensional simulation of the ligament during flexion-extension of the knee; and generating optimal locations of the ligament attachment points and of drill holes, to thereby allow a surgeon to plan a knee reconstruction procedure.

45. The method according to claim 44, further comprising generating at least one image including a representation of a ligament having an axis including a point of the femur and a point of the tibia.

* * * * *